United States Patent
Göttsche et al.

(10) Patent No.: US 10,420,339 B2
(45) Date of Patent: Sep. 24, 2019

(54) AQUEOUS FUNGICIDAL COMPOSITION AND USE THEREOF FOR COMBATING HARMFUL MICRO ORGANISMS

(71) Applicant: BASF SE, Ludwigshafen (DE)

(72) Inventors: Reimer Göttsche, Baden-Baden (DE); Gunnar Kleist, Baden-Baden (DE); Joerg Habicht, Sinzheim (DE); Holger Schöpke, Neckargemünd (DE); Patrick Amrhein, Hochheim (DE)

(73) Assignee: BASF SE, Ludwigshafen (DE)

( * ) Notice: Subject to any disclaimer, the term of this patent is extended or adjusted under 35 U.S.C. 154(b) by 103 days.

(21) Appl. No.: 15/397,555

(22) Filed: Jan. 3, 2017

(65) Prior Publication Data
US 2017/0112124 A1    Apr. 27, 2017

Related U.S. Application Data

(60) Continuation of application No. 14/261,193, filed on Apr. 24, 2014, now abandoned, which is a division of application No. 12/831,055, filed on Jul. 6, 2010, now Pat. No. 8,741,968, which is a division of application No. 11/587,052, filed as application No. PCT/EP2005/004423 on Apr. 25, 2005, now abandoned.

(30) Foreign Application Priority Data

Apr. 26, 2004 (DE) .................. 10 2004 020 332

(51) Int. Cl.
| | | |
|---|---|---|
| A01N 25/02 | (2006.01) | |
| A01N 25/04 | (2006.01) | |
| A01N 43/36 | (2006.01) | |
| A01N 43/653 | (2006.01) | |
| A01N 47/12 | (2006.01) | |
| C08L 97/02 | (2006.01) | |
| B27K 3/00 | (2006.01) | |
| B27K 3/15 | (2006.01) | |
| C08L 25/06 | (2006.01) | |
| C08L 33/14 | (2006.01) | |

(52) U.S. Cl.
CPC ............ *A01N 25/02* (2013.01); *A01N 25/04* (2013.01); *A01N 43/36* (2013.01); *A01N 43/653* (2013.01); *A01N 47/12* (2013.01); *C08L 97/02* (2013.01); *B27K 3/007* (2013.01); *B27K 3/15* (2013.01); *C08L 25/06* (2013.01); *C08L 33/14* (2013.01)

(58) Field of Classification Search
CPC .......... C08L 25/04; C08L 25/06; C08L 33/14; C08L 25/08–25/14; B27K 3/007; B27K 3/15

See application file for complete search history.

(56) References Cited

U.S. PATENT DOCUMENTS

| 5,922,398 A | 7/1999 | Hermes et al. |
|---|---|---|
| 2002/0051892 A1 | 5/2002 | Laks et al. |

FOREIGN PATENT DOCUMENTS

| CA | 2 543 553 | 5/2005 |
|---|---|---|
| EP | 1 230 855 | 8/2002 |
| WO | WO-99/65301 | 12/1999 |
| WO | WO-02/45507 | 6/2002 |
| WO | WO-02/082900 | 10/2002 |
| WO | WO-2005/046326 | 5/2005 |

OTHER PUBLICATIONS

Cyhalothrin MSDS, Syngenta last revised Mar. 31, 2005.
Derwent Publication, XP002342293, JP Application No. JPS58-72501 (English language Abstract), 1983, pp. 1-5.
Edifenphos MSDS, Sigma-Aldrich last revised Aug. 23, 2008.
Polymer Properties (Sigma Aldrich, "Thermal Transitions of Homopolymers: Glass Transition & Melting Point," accessed Sep. 18, 2012 via http://www.sigmaaldrich.com/img/assets/3900/Thermal_Transitions_of_Homopolymers.pdf, pp. 53-54).
Boehm, A.L.R. et al., "Poly Epsilon-Caprolactone Nanoparticles Containing a Poorly Soluble Pesticide: Formulation and Stability Study," Rapra Abstracts, Pergamon Press Ltd., Oxford, GB, vol. 37, No. 7, 2000, p. 120.
Liu, Y. et al., "Use of Nanoparticles for Controlled Release of Biocides in Solid Wood," Journal of Applied Polymer Science, vol. 79, No. 3, 2001, pp. 458-465.
Liu, Y. et al., "Controlled Release of Biocides in Solid Wood. I. Efficacy against Brown Rot Wood Decay Fungus (*Gloeophyllum trabeum*)," Journal of Applied Polymer Science, vol. 86, No. 3, 2002, pp. 596-607.

(Continued)

*Primary Examiner* — Kortney L. Klinkel
(74) *Attorney, Agent, or Firm* — Brinks Gilson & Lione

(57) ABSTRACT

The invention relates to aqueous fungicidal active substance compositions and to their use in the control of harmful microorganisms and in particular in the protection of cellulose-comprising materials, particularly wood, from infection by microorganisms, in particular those harmful fungi which can damage wood or cellulose.

The active substance composition according to the invention comprises:
  a) at least one fungicidal organic active substance with a solubility in water of not more than 5 g/l at 25° C./1013 mbar, and
  b) a finely-divided polymer with an average particle size, determined by dynamic light scattering, of not more than 300 nm, in which the polymer particles comprise the active substance, the polymer being formed from ethylenically unsaturated monomers M comprising:
    at least 60% by weight, based on the total amount of the monomers M, of at least one neutral monoethylenically unsaturated monomer M1 with a solubility in water of not more than 30 g/l at 25° C., and
    up to 40% by weight, based on the total amount of the monomers M, of one or more ethylenically unsaturated monomers M2 other than the monomers M1.

11 Claims, No Drawings

(56) References Cited

OTHER PUBLICATIONS

Liu, Y. et al., "Controlled Release of Biocides in Solid Wood. II. Efficacy against *Trametes versicolor* and *Gloeophyllum trabeum* Wood Decay Fungi," Journal of Applied Polymer Science, vol. 86, No. 3, 2002, pp. 608-614.

Liu, Y. et al., "Controlled Release of Biocides in Solid Wood. III. Preparation and Characterization of Surfactant-Free Nanoparticles," Journal of Applied Polymer Science, vol. 86, No. 3, 2002, pp. 615-621.

Page-Clissona, M.-E. et al., "Development of Ciprofloxacin-Loaded Nanoparticles: Physicochemical Study of the Drug Carrier," Journal of Controlled Release, 1998, vol. 56, Issues 1-3, pp. 23-32.

Pommer, E.H., Ullmann's Encyclopedia of Industrial Chemistry on CD-ROM, 5th ed., 1997, Wiley VCH, Weinheim. Wood Preservation, Chapter 2.3.1.

Shaw, D.J., "Introduction to Colloid and Surface Chemistry," Butterworth & Co., London, 1986, pp. 1-18 and 44-59.

AQUEOUS FUNGICIDAL COMPOSITION AND USE THEREOF FOR COMBATING HARMFUL MICRO ORGANISMS

CROSS-REFERENCE TO RELATED APPLICATIONS

This application is a Continuation of U.S. application Ser. No. 14/261,193, filed on Apr. 24, 2014, which is a Divisional of U.S. application Ser. No. 12/831,055, filed on Jul. 6, 2010 (now U.S. Pat. No. 8,741,968 on Jun. 3, 2014), which is a divisional of U.S. application Ser. No. 11/587,052, filed Oct. 20, 2006 (now abandoned). Application Ser. No. 11/587,052 is a National Stage Application of PCT International Application No. PCT/EP2005/004423, filed on Apr. 25, 2005. Priority is also claimed to German Application No. DE 102004020332.6, filed on Apr. 26, 2004. The entire contents of each of these applications is hereby incorporated by reference.

DESCRIPTION

The present invention relates to aqueous fungicidal active substance compositions and to their use in the control of harmful microorganisms, in particular for the protection of cellulose-comprising materials, in particular wood, from infection by harmful fungi, in particular those harmful fungi which may be harmful to wood or cellulose.

It is known that wood and also other cellulose-comprising materials can be attacked and in extreme cases destroyed by microorganisms and in particular fungi (subsequently harmful fungi) if they are exposed to environmental conditions which promote the growth and the development of such microorganisms. In addition, even if some types of wood have a natural resistance to such an infection, others, in particular types of softwood, are extremely susceptible to an infection (see also EN 350, Part 2). For this reason, wood is frequently treated with wood preservatives.

Conventional wood preservatives based on tar oils, such as carbolineum, are not very attractive because of their intrinsic smell and their potential carcinogenicity. Organic fungicides have on several occasions been proposed as wood preservatives (see E. H. Pommer in Ullmann's Encyclopedia of Industrial Chemistry on CD Rom, 5th edition, 1997, Wiley VCH, Weinheim, Wood preservation, chapter 2.3.1). Since the fungicidal active substances are usually substances which are insoluble in water, these are frequently formulated for the purposes of wood preservation as solutions in organic solvents. However, the use of solvents is associated with additional costs and, in addition, is undesirable for industrial hygiene reasons and for environmental protection reasons.

In plant protection, fungicidal active substances which exhibit only a low solubility in water are frequently formulated in the form of aqueous suspensions or emulsions. While emulsions usually still comprise organic solvents, suspensions are usually formulated free from solvents. The active substance is present in these suspensions in the form of fine particles with particle sizes in the micrometer region. If wood is now treated with such a suspension, the active substance remains on the surface of the wood since it, because of the particle size, cannot penetrate into the pores of the wood. However, this is required if effective protection of the wood is to be achieved. In addition, the active substance is easily washed off the surface by the effects of the weather.

Fungicidal transparent varnishes have also on several occasions been proposed as wood preservative. In this connection, these are aqueous painting systems based on aqueous polymer latexes which comprise the active substance in suspended form. Here again the protection of the wood is not satisfactory since the active substances do not penetrate into the wood but remain on the surface of the wood.

The proposal has been made on several occasions to formulate water-insoluble fungicidal active substances in the form of aqueous micro- or nanoemulsions (see, e.g., WO 02/082900, WO 02/45507 and WO 99/65301). In contrast to conventional, usually opaque, macroemulsions in which the disperse phase exhibits particle sizes clearly of greater than 1 μm, the active substances in the clear to opaque micro- or nanoemulsions are present in the finely divided form with particle sizes clearly of less than 1000 nm down to 10 nm or less [see in this connection D. J. Shaw, Introduction to Colloid and Surface Chemistry, Butterworths, London, 1986, p. 273]. Admittedly, comparatively large amounts of emulsifier and of organic solvents are necessary for the preparation of such micro- or nanoemulsions. Because of the high proportion of emulsifier, the danger exists that the active substance will be leached out, by the action of water, from the wood or the treated cellulose-comprising material. On the other hand, solvents are undesirable for industrial hygiene reasons and cost reasons. In addition, the water-absorbing capacity of the wood on exposure to moisture and the equilibrium moisture content on storage in a humid atmosphere are increased, in comparison with untreated wood, by the use of the emulsifiers, which makes the wood more susceptible to infection by harmful fungi. An additional problem of such microemulsions is their instability with regard to demixing. Such a demixing can, for example, occur if the microemulsion becomes depleted in emulsifier because of a high affinity of the emulsifier for the wood or a depletion in solvent occurs, which can easily happen in the pressure impregnation.

It is therefore an object of the present invention to provide an aqueous, fungicidally effective, composition of fungicidal active substances with low solubility in water, i.e. a solubility in water of less than 5 g/l, in particular less than 1 g/l, at 25° C./1013 mbar, which is advantageously suitable for the protection of cellulose-comprising materials, in particular wood, from infection by harmful fungi. The composition should in particular comprise only small amounts of or no volatile organic compounds, such as organic solvents. In addition, the active substance should not, or not to a significant extent, be leached from the treated materials by the effect of water. Furthermore, the aqueous active substance compositions should exhibit a better stability than conventional suspensions or microemulsions.

It has been found, surprisingly, that this object is achieved by an aqueous active substance composition in which the fungicidal active substance which is insoluble in water or only slightly soluble in water is present in the polymer particles of a finely divided water-insoluble polymer, the polymer particles of which exhibit a average particle size of not more than 300 nm, and in which the polymer is formed from at least 60% by weight, based on the total amount of the monomers M, of at least one neutral monoethylenically unsaturated monomer M1 with a solubility in water of not more than 30 g/l at 25° C. and up to 40% by weight, based on the total amount of the monomers M, of one or more ethylenically unsaturated monomers M2 other than the monomers M1.

Consequently, the present invention relates to an aqueous active substance composition, comprising:

a) at least one fungicidal organic active substance with a solubility in water of not more than 5 g/l at 25° C./1013 mbar, and b) a finely-divided polymer with an average particle size, determined by dynamic light scattering, of not more than 300 nm, in which the polymer particles comprise the active substance, the polymer being formed from ethylenically unsaturated monomers M comprising:

at least 60% by weight, based on the total amount of the monomers M, of at least one neutral monoethylenically unsaturated monomer M1 with a solubility in water of not more than 30 g/l at 25° C., and up to 40% by weight, based on the total amount of the monomers M, of one or more ethylenically unsaturated monomers M2 other than the monomers M1.

The compositions according to the invention are stable aqueous preparations of fungicidal active substances which are insoluble in water or only slightly soluble in water, which in principle are suitable for all applications in which it is desired to achieve effective protection from infection by microorganisms, in particular harmful fungi.

In spite of the incorporation of the fungicidal active substance in a polymer matrix, the rate of application of active substance necessary for effective protection is, surprisingly, not higher and in a few cases even lower than when conventional aqueous active substance preparations are used.

The present invention also relates to the use of such aqueous compositions for the control of microorganisms, in particular for the control of harmful fungi. The term "control" comprises, here and subsequently, the prevention or avoidance of infection by microorganisms, in particular harmful fungi and also the destruction of microorganisms, in particular harmful fungi, in infected substrates.

The compositions according to the invention are particularly suitable for the control of microorganisms, in particular of harmful fungi, in wood and other cellulose materials and in particular for the protection of these materials from infection by microorganisms, in particular harmful fungi. Hence, a particular embodiment of the invention relates to the use of such compositions for the protection of cellulose-comprising materials from infection by microorganisms, in particular from infection by wood-destroying fungi.

However, the aqueous compositions according to the invention are also suitable for other applications in which control of microorganisms, in particular harmful fungi, is desired, for example in plant protection, for the control of phytotoxic microorganisms, in seed treatment, and also in the protection of materials, as in-can and film preservatives, for antifouling, and for the protection of leather and other organic materials from infection by harmful microorganisms.

The particle sizes of the finely divided polymer given here are weight-average particle sizes, as can be determined by dynamic light scattering. Methods for this are familiar to a person skilled in the art, for example from H. Wiese in D. Distler, Wassrige Polymerdispersionen [Aqueous Polymer Dispersions], Wiley-VCH, 1999, chapter 4.2.1, p. 40ff and the literature cited therein, and also H. Auweter, D. Horn, J. Colloid Interf. Sci., 105 (1985), 399, D. Lilge, D. Horn, Colloid Polym. Sci., 269 (1991), 704, or H. Wiese, D. Horn, J. Chem. Phys., 94 (1991), 6429. The average particle size preferably ranges from 10 to 250 nm, in particular from 20 to 200 nm, particularly preferably from 30 to 150 nm and very particularly preferably from 30 to 100 nm.

The polymer is, according to the invention, at least 60% by weight, based on the total amount of the monomers M forming the polymer, preferably 60 to 99.5% by weight and particularly preferably 70 to 99% by weight formed from neutral monoethylenically unsaturated monomers M1 with a solubility in water of not more than 30 g/l at 25° C./1013 mbar. In particular, the solubility in water of the monomers M1 under these conditions is from 0.1 to 20 g/l. Suitable monomers M1 comprise vinylaromatic monomers, such as styrene, esters of monoethylenically unsaturated mono- and dicarboxylic acids with 3 to 8 and in particular 3 or 4 carbon atoms with $C_1$-$C_{10}$-alkanols or with $C_5$-$C_8$-cycloalkanols, in particular the esters of acrylic acid, of methacrylic acid or of crotonic acid, the diesters of maleic acid, of fumaric acid and of itaconic acid, and particularly preferably the esters of acrylic acid with $C_2$-$C_{10}$-alkanols (=$C_2$-$C_{10}$-alkyl acrylates), such as ethyl acrylate, n-butyl acrylate, isobutyl acrylate, tert-butyl acrylate, n-hexyl acrylate, 2-ethylhexyl acrylate and 3-propylheptyl acrylate, and the esters of methacrylic acid with $C_1$-$C_{10}$-alkanols, such as methyl methacrylate, ethyl methacrylate, n-butyl methacrylate, isobutyl methacrylate, tert-butyl methacrylate, n-hexyl methacrylate and the like. Suitable monomers M1 are, in addition, vinyl and allyl esters of aliphatic carboxylic acids with 2 to 10 carbon atoms, for example vinyl acetate, vinyl propionate and the vinyl esters of Versatic® acids (vinyl versatate), vinyl halides, such as vinyl chloride and vinylidene chloride, conjugated diolefins, such as butadiene and isoprene, and $C_2$-$C_6$-olefins, such as ethylene, propene, 1-butene and n-hexene.

Preferred monomers M1 are vinylaromatic monomers, in particular styrene, $C_2$-$C_{10}$-alkyl acrylates, in particular $C_2$-$C_8$-alkyl acrylates, and $C_1$-$C_{10}$-alkyl methacrylates.

The ethylenically unsaturated monomers M which form the polymer advantageously also comprise at least 0.5 to 40% by weight, in particular 1 to 30% by weight, of at least one ethylenically unsaturated monomer M2 other than the monomers M1.

The monomers M2 include in particular monoethylenically unsaturated monomers M2a exhibiting at least one acid group or at least one anionic group, in particular monomers M2a exhibiting a sulfonic acid group, a phosphonic acid group or one or two carboxylic acid groups, and the salts of the monomers M2a, in particular the alkali metal salts, e.g. the sodium or potassium salts, and the ammonium salts. These include ethylenically unsaturated sulfonic acids, in particular vinylsulfonic acid, 2-acrylamido-2-methylpropanesulfonic acid, 2-acryloxyethanesulfonic acid, 2-methacryloxyethanesulfonic acid, 3-acryloxy- and 3-methacryloxypropanesulfonic acid, vinylbenzenesulfonic acid and their salts, ethylenically unsaturated phosphonic acids, such as vinylphosphonic acid and vinylphosphonic acid dimethyl ester and their salts, and α,β-ethylenically unsaturated $C_3$-$C_8$-mono- and $C_4$-$C_5$-dicarboxylic acids, in particular acrylic acid, methacrylic acid, crotonic acid, maleic acid, fumaric acid and itaconic acid. The proportion of the monomers M2a will commonly come to not more than 35% by weight, preferably not more than 20% by weight, e.g. 0.1 to 20% by weight and in particular 0.5 to 15% by weight, based on the total amount of the monomers M.

The monomers M2 additionally include monoethylenically unsaturated neutral monomers M2b exhibiting a solubility in water of at least 50 g/l at 25° C. and in particular of at least 100 g/l at 25° C. Examples of these are the amides of the abovementioned ethylenically unsaturated carboxylic acids, in particular acrylamide and methacrylamide, ethylenically unsaturated nitriles, such as methacrylonitrile and acrylonitrile, hydroxyalkyl esters of the abovementioned α,β-ethylenically unsaturated $C_3$-$C_8$-monocarboxylic acids and $C_4$-$C_8$-dicarboxylic acids, in particular hydroxyethyl acrylate, hydroxyethyl methacrylate, 2- and 3-hydroxypropyl acrylate, and 2- and 3-hydroxypropyl methacrylate, and esters of the abovementioned monoethylenically unsaturated mono- and dicarboxylic acids with $C_2$-$C_4$-polyalkylene glycols, in particular the esters of these carboxylic acids with polyethylene glycol or alkylpolyethylene glycols, the (alkyl) polyethylene glycol residue usually exhibiting a molecular weight ranging from 100 to 3000. The monomers M2b furthermore include N-vinylamides, such as N-vinylformamide, N-vinylpyrrolidone, N-vinylimidazole and N-vinylcaprolactam. The proportion of the monomers M2b will preferably come to not more than 20% and in particular not more than 10% by weight, e.g. 0.1 to 10 and in particular 0.5 to 5% by weight, based on the total amount of the monomers M.

The monomers M2 furthermore include monoethylenically unsaturated monomers M2c exhibiting at least one cationic group and/or at least one group which can be protonated in the aqueous medium. The monomers M2c include in particular those exhibiting a protonatable amino group, a quaternary ammonium group, a protonatable imino group or a quatemized imino group. Examples of monomers with a protonatable imino group are N-vinylimidazole and vinylpyridines. Examples of monomers with a quatemized imino group are N-alkylvinylpyridinium salts and N-Alkyl-N'-vinylimidazolinium salts, such as N-methyl-N'-vinylimidazolinium chloride or methyl sulfate. Preference is given, among the monomers M2c, in particular to the monomers of the general formula (I)

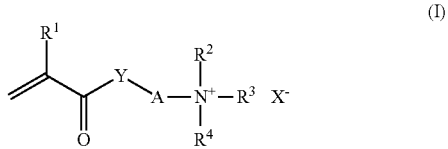

(I)

in which
$R^1$ is hydrogen or $C_1$-$C_4$-alkyl, in particular hydrogen or methyl,
$R^2$ and $R^3$ are, independently of one another, $C_1$-$C_4$-alkyl, in particular methyl, and
$R^4$ is hydrogen or $C_1$-$C_4$-alkyl, in particular hydrogen or methyl,
Y is oxygen, NH or $NR^5$ with $R^5$=$C_1$-$C_4$-alkyl,
A is $C_2$-$C_8$-alkylene, e. g. 1,2-ethanediyl, 1,2- or 1,3-propanediyl, 1,4-butanediyl or 2-methyl-1,2-propanediyl, if appropriate interrupted by 1, 2 or 3 nonadjacent oxygen atoms, and
$X^-$ is an anion equivalent, e.g. $Cl^-$, $HSO_4^-$, $\frac{1}{2}SO_4^{2-}$ or $CH_3OSO_3^-$, and the like, and, for $R^4$=H, the free bases of the monomers of the formula I.

Examples of such monomers are 2-(N,N-dimethylamino) ethyl acrylate, 2-(N,N-dimethylamino)ethyl methacrylate, 2-(N,N-dimethylamino)ethylacrylamide, 3-(N,N-dimethylamino)propylacrylamide, 3-(N,N-dimethylamino)propylmethacrylamide, 2-(N,N-dimethylamino)ethylmethacrylamide, 2-(N,N,N-trimethylammonio)ethyl acrylate chloride, 2-(N,N,N-trimethylammonio)ethyl methacrylate chloride, 2-(N,N,N-trimethylammonio)ethylmethacrylamide chloride, 3-(N,N,N-trimethylammonio)propylacrylamide chloride, 3-(N,N, N-trimethylammonio)propylmethacrylamide chloride, 2-(N,N,N-trimethylammonio)ethylacrylamide chloride, and the corresponding sulfates and methyl sulfates.

In a preferred embodiment, the monomers M which form the polymer comprise at least one monomer M2c. The proportion of the monomers M2c is then advantageously 0.1 to 20% by weight, in particular 0.5 to 10% by weight and particularly preferably 1 to 7% by weight, based on the total amount of the monomers M.

In a particularly preferred embodiment of the invention, the polymer exhibits a net cationic charge, i.e. the molar proportion of the monomers M2c is greater than the molar proportion of the monomers M2a in the polymer and is preferably 110 mol %, in particular at least 120 mol % and particularly preferably at least 150 mol %, based on the monomers M2a.

The monomers M2 furthermore include all monomers which can conventionally be used in an emulsion polymerization. However, the proportion of monomers exhibiting two or more nonconjugated ethylenically unsaturated double bonds usually comes to not more than 5% by weight, in particular not more than 2% by weight, e.g. 0.01 to 2% by weight and in particular 0.05 to 1.5% by weight, based on the total amount of monomers.

Furthermore, it has proved to be advantageous for the polymer present in the compositions according to the invention to exhibit a glass transition temperature $T_g$ of at least 10° C., preferably of at least 20° C. and in particular of at least 30° C. In particular, the glass transition temperature will not exceed a value of 180° C. and particularly preferably 130° C. If the active substance composition according to the invention comprises several polymers with different glass transition temperatures, be it in the form of step or core/shell polymers or in the form of blends of different polymers, the proportion of polymers with a glass transition temperature of at least 10° C., preferably at least 20° C. and in particular at least 30° C. is at least 40% by weight.

The term "glass transition temperature $T_g$" is to be understood here as the midpoint temperature determined by differential scanning calorimetry (DSC) according to ASTM D 3418-82 (cf. Ullmann's Encyclopedia of Industrial Chemistry, 5th edition, volume A 21, VCH, Weinheim, 1992, p. 169, and Zosel, Farbe und Lack, 82 (1976), p. 125-134, see also DIN 53765).

In this connection, it proves to be helpful to estimate the glass transition temperature $T_g$ of the copolymer P. According to Fox (T. G. Fox, Bull. Am. Phys. Soc. (Ser. II), 1, 123 [1956] and Ullmann's Encyclopedia of Industrial Chemistry, Weinheim (1980), p. 17-18), the following equation $$\frac{1}{T_g} = \frac{X^1}{T_g^1} + \frac{X^2}{T_g^2} + \ldots \frac{X^n}{T_g^n}$$

is, to a good approximation, valid for the glass transition temperature of weakly crosslinked copolymers with high molar masses, in which equation $X^1, X^2, \ldots, X^n$ represent the mass fractions of the monomers 1, 2, ..., n and $T_g^1$, $T_g^2, \ldots, T_g^n$ represent, in degrees Kelvin, the glass transition temperatures of the polymers formed in each case only from one of the monomers 1, 2, ..., n. The latter are, e.g., known from Ullmann's Encyclopedia of Industrial Chemistry, VCH, Weinheim, Vol. A 21, (1992) p. 169, or from J. Brandrup, E. H. Immergut, Polymer Handbook, 3rd ed., J. Wiley, New York, 1989.

All organic substances with low solubility in water which inhibit the growth or the propagation of harmful fungi or which destroy the latter are suitable in principle as active substances. Their solubility in water at 25° C./1013 mbar is generally not more than 5 g/l, frequently not more than 3 g/l and in particular not more than 1 g/l, e. g. 0.001 g/l to 1 g/l, in particular 0.002 to 0.5 g/l, at 25° C./1013 mbar.

Examples of suitable active substances are the compounds listed as fungicides in the Compendium of Pesticide Common Names: http://www.hclrss.demon.co.uk/class-fungicides.html (Index of common names). These include, for example:

acylalanines, such as benalaxyl, metalaxyl, ofurace or oxadixyl;

morpholine compounds, such as aldimorph, dodine, dodemorph, fenpropimorph, fenpropidin, guazatine, iminoctadine, spiroxamine or tridemorph;

anilinopyrimidines, such as pyrimethanil, mepanipyrim or cyprodinil;

antibiotics, such as cycloheximide, griseofulvin, kasugamycin, natamycin, polyoxin or streptomycin;

azoles, such as azaconazole, bitertanol, bromoconazole, cyproconazole, diclobutrazol, difenoconazole, diniconazole, epoxiconazole, fenbuconazole, fluquinconazole, flusilazole, flutriafol, ketoconazole, hexaconazole, imazalil, metconazole, myclobutanil, penconazole, propiconazole, prochloraz, prothioconazole, tebuconazole, tetraconazole, triadimefon, triadimenol, triflumizole or triticonazole;

dicarboximides, such as iprodione, myclozolin, procymidone or vinclozolin;

dithiocarbamates, such as ferbam, nabam, maneb, mancozeb, metam, metiram, propineb, polycarbamate, thiram, ziram or zineb;

heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine;

nitrophenyl derivatives, such as binapacryi, dinocap, dinobuton or nitrothal-isopropyl;

phenylpyrroles, such as fenpiclonil or fludioxonil;

strobilurins, such as dimoxystrobin, fluoxastrobin, kresoxim-methyl, metominostrobin, orysastrobin, picoxystrobin, pyraciostrobin and trifloxystrobin;

other fungicides, such as acibenzolar-S-methyl, benzoyl-benzoate, dodecylguanidine hydrochloride, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide;

sulfenic acid derivatives, such as captafol, captan, dichlofluanid, folpet or tolylfluanid;

cinnamamides and analogous compounds, such as dimethomorph, flumetover or flumorph.

These furthermore include:

iodine compounds, such as diiodomethyl p-tolyl sulfone, 3-iodo-2-propynyl alcohol, 4-chlorophenyl-3-iodopropargylformal, 3-bromo-2,3-diiodo-3-propenyl ethyl carbonate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl phenylcarbamate, O-1-(6-iodo-3-oxohex-5-ynyl) butylcarbamate, O-1-(6-iodo-3-oxohex-5-ynyl) phenylcarbamate or napcocide;

phenol derivatives, such as tribromophenol, tetrachlorophenol, 3-methyl-4-chlorophenol, dichlorophen, o-phenylphenol, m-phenylphenol or 2-benzyl-4-chlorophenol;

isothiazolinones, such as N-methylisothiazolin-3-one, 5-chloro-N-methyl-isothiazolin-3-one, 4,5-dichloro-N-octylisothiazolin-3-one or N-octylisothiazolin-3-one;

(benz)isothiazolinones, such as 1,2-benzisothiazol-3(2H)-one, 4,5-trimethylisothiazol-3-one or 2-octyl-2H-isothiazol-3-one;

pyridines, such as 1-hydroxy-2-pyridinethione (and its Na, Fe, Mn and Zn salts), or tetrachloro-4-methylsulfonylpyridine;

metal soaps, such as tin, copper or zinc naphthenate, octoate, 2-ethylhexanoate, oleate, phosphate or benzoate;

organotin compounds, e.g. tributyltin (TBT) compounds, such as tributyltin and tributyl(mononaphthenoyloxy) tin derivatives;

dialkyldithiocarbamates and the Na and Zn salts of dialkyldithiocarbamates, tetramethylthiouram disulfide;

nitriles, such as 2,4,5,6-tertrachloroisophthalodinitrile;

benzthiazoles, such as 2-mercaptobenzothiazole;

quinolines, such as 8-hydroxyquinoline, and their Cu salts;

tris-(N-cyclohexyldiazeniumdioxy)aluminum, (N-cyclohexyldiazeniumdioxy)-tributyltin, or bis(N-cyclohexyldiazeniumdioxy)copper;

3-benzo[b]thien-2-yl-5,6-dihydro-1,4,2-oxathiazine 4-oxide (bethoxazin).

With regard to the use of the compositions according to the invention for the protection of cellulose-comprising materials from infection by microorganisms of relevance in wood preservation, mainly molds, wood-discoloring fungi and wood-destroying fungi, preference is given in particular to those fungicides which are effective, for example, against the following groups of microorganisms:

wood-discoloring fungi:

ascomycetes, such as *Ophiostoma* sp. (e.g. *Ophiostoma piceae, Ophiostoma piliferum*), *Ceratocystis* sp. (e.g. *Ceratocystis coerulescens*), *Aureobasidium pullulans* or *Sclerophoma* sp. (e.g. *Sclerophoma pityophila*);

deuteromycetes, such as *Aspergillus* sp. (e.g. *Aspergillus niger*), *Cladosporium* sp. (e.g. *Cladosporium sphaerospermum*), *Penicillium* sp. (e.g. *Penicillium funiculosum*), *Trichoderma* sp. (e.g. *Trichoderma viride*), *Alternaria* sp. (e.g. *Altemaria altemata*) or *Paecilomyces* sp. (e.g. *Paecilomyces variotii*);

zygomycetes, such as *Mucor* sp. (e.g. *Mucor hiemalis*);

Wood-destroying fungi:

ascomycetes, such as *Chaetomium* sp. (e.g. *Chaetomium globosum*), *Humicola* sp. (e.g. *Humicola grisea*), *Petriella* sp. (e.g. *Petriella setifera*) or *Trichurus* sp. (e.g. *Trichurus spiralis*);

basidiomycetes, such as *Coniophora* sp. (e.g. *Coniophora puteana*), *Coriolus* sp. (e.g. *Coriolus versicolor*), *Gloeophyllum* sp. (e.g. *Gloeophyllum trabeum*), *Lentinus* sp. (e.g. *Lentinus lepideus*), *Pleurotus* sp. (e.g. *Pleurotus ostreatus*), *Poria* sp. (e.g. *Poria placenta, Poria vaillantii*), *Serpula* sp. (e.g. *Serpula lacrymans*) and *Tyromyces* sp. (e.g. *Tyromyces palustris*), Preferred active substances are hence selected from the group of the conazoles, the group of the morpholines, the group of the strobilurins, the group of the thiazoles, the group of the sulfenamides and the group of the iodine compounds.

Preference is given in particular to those fungicides mentioned in category 08 (wood preservatives) in the biocide regulation of the European Union (COMMISSION REGULATION (EC) No. 2032/2003 of Nov. 4, 2003).

The aqueous active substance preparations according to the invention comprise the fungicidal active substance generally in an amount of 0.1 to 50% by weight, preferably in an amount of 0.2 to 30% by weight and in particular in an amount of 0.5 to 20% by weight, based on the polymer present in the composition or based on the total amount of the monomers M used to prepare the polymer.

In addition to the fungicidal active substance, the compositions according to the invention can also comprise one or more insecticidal active substances. In a preferred embodiment, the insecticidal active substances, together with the at least one fungicidal active substance, are present in the polymer particles. The insecticidal active substance is then preferably an organic active substance with a low solubility in water generally of not more than 5 g/l, preferably not more than 3 g/l and in particular not more than 1 g/l, e.g. 0.001 to 1 g/l or 0.002 to 0.5 g/l, at 25° C./1013 mbar. Examples of suitable insecticidal active substances are the compounds listed as insecticides in the Compendium of Pesticide Common Names: http://www.hclrss.demon.co.uk/class-insecticides.html (Index of common names).

These include, for example:

organo(thio)phosphates, such as acephate, azamethiphos, azinphos-methyl, chlorpyrifos, chlorpyriphos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos or trichlorfon;

carbamates, such as alanycarb, benfuracarb, bendiocarb, carbaryl, carbosulfan, fenoxycarb, furathiocarb, indoxacarb, methiocarb, methomyl, oxamyl, pirimicarb, propoxur, thiodicarb or triazamate;

pyrethroids, such as allethrin, bifenthrin, cyfluthrin, cyphenothrin, cypermethrin, and the alpha-, beta-, theta- und zeta-isomers, deltamethrin, esfenvalerate, ethofenprox, fenpropathrin, fenvalerate, cyhalothrin, lambda-cyhalothrin, imiprothrin, permethrin, prallethrin, pyrethnn I, pyrethrin II, silafluofen, tau-fluvalinate, tefluthrin, tetramethrin, tralomethrin, transfluthrin or zeta-cypermethrin;

arthropod growth regulators, such as a) chitin synthesis inhibitors; e.g. benzoylureas, such as chlorfluazuron, cyromacin, diflubenzuron, flucycloxuron, flufenoxuron, hexaflumuron, lufenuron, novaluron, teflubenzuron, triflumuron; buprofezin, diofenolan, hexythiazox, etoxazole or clofentezine; b) ecdysone antagonists, such as halofenozide, methoxyfenozide or tebufenozide;

c) juvenoids, such as pyriproxyfen, methoprene or fenoxycarb;

d) lipid biosynthesis inhibitors, such as spirodiclofen;

neonicotinoids, such as flonicamid, clothianidin, dinotefuran, imidacloprid, thiamethoxam, nitenpyram, nithiazine, acetamiprid or thiacloprid;

pyrazole insecticides, such as acetoprole, ethiprole, fipronil, tebufenpyrad, tolfenpyrad and vaniliprole.

in addition, abamectin, acequinocyl, amitraz, azadirachtin, bifenazate, cartap, chlorfenapyr, chlordimeform, cyromazine, diafenthiuron, diofenolan, emamectin, endosulfan, fenazaquin, formetanate, formetanate hydrochloride, hydramethylnon, indoxacarb, piperonyl butoxide, pyridaben, pymetrozine, spinosad, thiamethoxam, thiocyclam, pyridalyl, fluacyprim, milbemectin, spiro-mesifen, flupyrazofos, NCS 12, flubendiamide, bistrifluron, benclothiaz, pyrafluprole, pyriprole, amidoflumet, flufenerim, cyflumetofen, lepimectin, profluthrin, dimefluthrin and metaflumizone.

Preference is given, among these, to those insecticides which are effective against wood-destroying insects and in particular against the following wood-destroying insects:

Order Coleoptera (beetles):
  Cerambycidae, such as *Hylotrupes bajulus* or *Callidium violaceum;*
  Lyctidae, such as *Lyctus linearis* or *Lyctus brunneus;*
  Bostrichidae, such as *Dinoderus minutus;*
  Anobiidae, such as *Anobium punctatum* or *Xestobium rufovillosum;*
  Lymexylidae, such as *Lymexylon navale;*
  Platypodidae, such as *Platypus cylindrus;*
  Oedemeridae, such as *Nacerda melanura;*

Order Hymenoptera (hymenopterans):
  Formicidae, such as *Camponotus abdominalis, Lasius flavus, Lasius brunneus* or *Lasius fuliginosus;*

Order Isoptera (termites):
  Kalotermitidae, such as *Kalotermes flavicollis* or *Cryptothermes brevis;*
  Hodotermitidae, such as *Zootermopsis angusticollis* or *Zootermopsis nevadensis;*
  Rhinotermitidae, such as *Reticulitermes flavipes, Reticulitermes lucifugus, Coptotermes formosanus* or *Coptotermes acinaciformis;*
  Mastotermitidae, such as *Mastotermes darwiniensis.*

These include in particular the insecticidal active substances from the class of the pyrethroids, arthropod growth regulators, such as chitin biosynthesis inhibitors, ecdysone antagonists, juvenoids or lipid biosynthesis inhibitors, neonicotinoids, pyrazole insecticides and chlorfenapyr.

Preference is given in particular to those insecticidal active substances mentioned in category 08 (wood preservatives) and category 18 (insecticides, acaricides and products to control other arthropods) in the biocide regulation of the European Union (COMMISSION REGULATION (EC) No. 2032/2003 of Nov. 4, 2003).

The insecticidal active substance is, if desired, usually present in the active substance composition according to the invention in an amount of 0.1 to 50% by weight, preferably in an amount of 0.2 to 30% by weight and in particular in an amount of 0.5 to 20% by weight, based on the monomers M which form the polymer.

The total amount of active substance in the polymer of the compositions according to the invention is preferably 0.2 to 50% by weight, in particular 0.5 to 30% by weight and particularly preferably 1 to 20% by weight, based on the polymer or on the monomers M which form the polymer.

The aqueous compositions according to the invention usually comprise surface-active substances in order to stabilize the polymer particles in the aqueous medium. These include both protective colloids and low-molecular-weight emulsifiers, the latter, in contrast to the protective colloids, generally exhibiting a molecular weight of less than 2000 g/mol, in particular of less than 1000 g/mol (weight-average). The protective colloids and emulsfiers can be both cationic, anionic or neutral in nature and zwitterionic in nature.

Examples of anionic surface-active substances are anionic emulsifiers, such as alkylphenylsulfonates, phenylsulfonates, alkyl sulfates, alkylsulfonates, alkyl ether sulfates, alkylphenol ether sulfates, alkyl polyglycol ether phosphates, alkyldiphenyl ether sulfonates, polyarylphenyl ether phosphates, alkyl sulfosuccinates, olefin sulfonates, paraffin sulfonates, petroleum sulfonates, taurides, sarcosides, fatty acids, alkylnaphthalenesulfonic acids or naphthalenesulfonic acids, including their alkali metal, alkaline earth metal, ammonium and amine salts. Examples of anionic protective colloids are lignosulfonic acids, condensation products of sulfonated naphthalenes with formaldehyde or with formaldehyde and phenol and, if appropriate, urea, and also condensation products from phenolsulfonic acid, formaldehyde and urea, lignin sulfite waste liquor and lignosulfonates, and also polycarboxylates, such as polyacrylates, maleic anhydride/olefin copolymers (e.g. Sokalan® CP9, BASF), and also the alkali metal, alkaline earth metal, ammonium and amine salts of the abovementioned protective colloids.

Nonionic emulsifiers are, for example, alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkylpolyglycosides and glycerol fatty acid esters. Examples of nonionic protective colloids are polyethylene glycol, polypropylene glycol, polyethylene glycollpolypropylene glycol block copolymers, polyethylene glycol alkyl ethers, polypropylene glycol alkyl ethers, polyethylene glycol/polypropylene glycol ether block copolymers, and their mixtures.

Examples of cationic emulsifiers are quaternary ammonium salts, e.g. trimethyl- and triethyl($C_6$-$C_{30}$-alkyl)ammonium salts, such as cocotrimethylammonium salts and trimethylcetylammonium salts, dimethyl- and diethyldi($C_4$-$C_{20}$-alkyl)ammonium salts, such as didecyldimethylammonium salts and dicocodimethylammonium salts, methyl- and ethyltri($C_4$-$C_{20}$-alkyl)ammonium salts, such as methyttrioctylammonium salts, ($C_1$-$C_{20}$-alkyl)di($C_1$-$C_4$-alkyl)benzylammonium salts, such as triethylbenzylammonium salts and cocobenzyldimethylammonium salts, methyl- and ethyldi ($C_4$-$C_{20}$-alkyl)poly(oxyethyl)ammonium salts, e.g. didecylmethylpoly(oxyethyl)ammonium salts, N—($C_6$-$C_{20}$-alkyl) pyridinium salts, e.g. N-laurylpyridinium salts, N-methyl- and N-ethyl-N—($C_8$-$C_{20}$-alkyl)morpholinium salts, and N-methyl- and N-ethyl-N'—($C_6$-$C_{20}$-alkyl)imidazolinium salts, in particular the halides, borates, carbonates, formates, acetates, propionates, hydrogencarbonates, sulfates and methyl sulfates.

Examples of cationic protective colloids are homo- and copolymers of the abovementioned monomers M2c with a content of monomers M2c of at least 20% by weight, in particular at least 30% by weight of monomers M2c, for example homopolymers of N-vinyl-N-methylimidazolinium salts or of N-alkylvinylpyridinium salts and copolymers of these monomers with neutral monomers M2b which are preferably miscible with water.

Zwitterionic emulsifiers are those with betaine structures. Such substances are known to a person skilled in the art and can be taken from the relevant state of the art (see, for example, R. Heusch, in Ullmann's Encyclopedia of Industrial Chemistry, 5th ed., on CD-ROM, Wiley-VCH, 1997, "Emulsions", chapter 7, Table 4).

The compositions according to the invention usually comprise at least one emulsifier, preferably at least one ionic emulsifier and, if appropriate, one or more nonionic emulsifiers. With regard to the application in wood preservation, it has proved worthwhile for the compositions according to the invention to comprise at least one cationic emulsifier, in particular if no monomers M2c are used to prepare the polymer.

The amount of emulsifier usually ranges from 0.1 to 15% by weight, in particular from 0.2 to 12% by weight and particularly preferably from 0.7 to 10% by weight, based on the monomers M or on the polymer P. The amount of ionic emulsifier is preferably 0.3 to 10% by weight and in particular 0.5 to 8% by weight, based on the monomers M constituting the polymer. The amount of nonionic emulsifier preferably ranges from 0.2 to 12% by weight, in particular from 0.5 to 10% by weight, based on the monomers M constituting the polymer.

The preparation of the aqueous compositions according to the invention comprises a radical aqueous emulsion polymerization of an oil-in-water emulsion of the monomers M, in which the monomer droplets of the emulsion comprise at least one fungicidal active substance and, if appropriate, an insecticidal active substance. The polymerization is carried out analogously to a conventional emulsion polymerization, with the difference that the monomer emulsion to be polymerized comprises the active substance dissolved in the monomer droplets.

The oil-in-water emulsion of the active substance/monomer solution can be prepared in situ by addition of a solution of the active substance in the monomers M to be polymerized in the polymerization vessel placed under polymerization conditions. However, preferably, the active substance will be dissolved in the monomers M and the monomer solution thus obtained will be converted to an aqueous monomer emulsion, before the monomerlactive substance emulsion thus obtained is fed to the polymerization reaction.

The polymerization is generally carried out according to a "monomer feed process", i.e. the greater part, preferably at least 70% and in particular at least 90%, of the solution of the active substance in the monomers M or the greater part, preferably at least 70% and in particular at least 90%, of the monomer/active substance emulsion is fed to the polymerization vessel in the course of the polymerization reaction. The addition of the monomer/active substance solution or emulsion is preferably carried out over a period of at least 0.5 h, preferably at least 1 h, e.g. 1 to 10 h and in particular 2 to 5 h. The addition of the monomer/active substance solution or emulsion can be carried out with a constant or variable addition rate, e.g. in intervals with a constant addition rate or with a variable addition rate or continuously with a variable addition rate. The composition of the monomer/active substance solution or emulsion can remain constant during the addition or can be changed, it being possible for changes to be made both with regard to the monomer composition and with regard to the type of active substance or the concentration of the active substance.

In a preferred embodiment of the invention, the monomer composition is changed in the course of the monomer addition in such a way that polymer regions with a different glass transition temperature are obtained in the polymer particles. This is achieved by a "step polymerization". For this, first, a first monomer/active substance solution or emulsion, the monomer composition of which corresponds to a glass transition temperature $T_g^1$, is polymerized in a first step and subsequently a second monomer/active substance solution or emulsion, the monomer composition of which corresponds to a glass transition temperature $T_g^2$, is provided for this (2nd step) and, if appropriate, subsequent thereto, successively one or more additional monomer/active substance solutions or emulsions, the monomer composition of which corresponds in each case to a glass transition temperature $T_g^n$, n being the respective step, is/are provided for this. The respective glass transition temperatures in polymers obtained in successive polymerization steps preferably differ by at least 10 K, in particular by at least 20 K and particularly preferably by at least 30 K, e.g. 30 K to 200 K, in particular 40 K to 160 K. Generally, the monomer amount polymerized in a monomer amount will come to at least 5% by weight, preferably at least 10% by weight, e.g. 5 to 95% by weight, in particular 10 to 90% by weight, in a 2-step polymerization and 5 to 90 or 5 to 85% by weight, in particular 10 to 80% by weight, in a polymerization with three or more steps.

It has proved to be advantageous, for the preparation of the active substance composition according to the invention and for the properties of the active substance composition, for the emulsion polymerization to be carried out in the presence of a seed polymer (seed latex). In this connection, it is a finely divided polymer latex, the average particle size of which is usually not more than 100 nm, in particular not more than 80 nm and particularly preferably not more than 50 nm. The monomers constituting the seed latex are preferably to at least 90% by weight, in particular to at least 95% by weight and frequently to more than 99% by weight selected from the monomers M1, the seed latex also being able to comprise, for the stabilization, small amounts, e.g. 0.1 to 10% by weight, in particular 0.1 to 5% by weight and especially 0.1 to 1% by weight, thereof different monomers M2, e.g. monomers M2a. The seed latex frequently exhibits a glass transition temperature of at least 10, in particular of at least 50 and frequently of at least 80° C. The amount of seed latex is usually 0.01 to 5% by weight, in particular 0.1 to 4% by weight, based on the monomers M1 to be polymerized. Preferably, the bulk, and in particular all, of the seed latex is found, at the beginning of the polymerization, completely in the reaction vessel. The seed latex can also be generated in situ in the polymerization vessel by radical emulsion polymerization of the monomers which form the seed latex, the monomers which form the seed latex being selected from the abovementioned monomers M1 and M2 and in particular to at least 90% by weight from the monomers M1. The desired particle size of the seed latex can be controlled in a way known per se via the ratio of monomer to emulsifier.

The initiators suitable for the emulsion polymerization according to the invention are the polymerization initiators suitable for and conventionally used for an emulsion polymerization which initiate a radical polymerization of the monomers M. These include azo compounds, such as 2,2'-azobisisobutyronitrile, 2,2'-azobis(2-methyl-butyronitrile), 2,2'-azobis[2-methyl-N-(2-hydroxyethyl)propionamide], 1,1'-azobis(1-cyclohexanecarbonitrile), 2,2'-azobis(2,4-dimethylvaleronitrile), 2,2'-azobis(N,N'-dimethyleneisobutyramidine) dihydrochloride and 2,2'-azobis(2-amidinopropane) dihydrochloride, organic or inorganic peroxides, such as diacetyl peroxide, di(tert-butyl) peroxide, diamyl peroxide, dioctanoyl peroxide, didecanoyl peroxide, dilauroyl peroxide, dibenzoyl peroxide, bis(o-toluyl) peroxide, succinyl peroxide, tert-butyl peracetate, tert-butyl permaleate, tert-butyl perisobutyrate, tert-butyl perpivalate, tert-butyl peroctoate, tert-butyl pemeodecanoate, tert-butyl perbenzoate, tert-butyl peroxide, tert-butyl hydroperoxide, cumene hydroperoxide, tert-butyl peroxy(2-ethylhexanoate) and diisopropyl peroxydicarbamate, salts of peroxydisulfuric acid and redox initiator systems.

Use is preferably made of water-soluble initiators, e.g. cationic azo compounds, such as azobis(dimethylamidinopropane), salts of peroxydisulfuric acid, in particular a sodium, potassium or ammonium salt, or a redox initiator system, which a salt of peroxydisulfuric acid, hydrogen peroxide or an organic peroxide, such as tert-butyl hydroperoxide, as oxidizing agent. As reducing agent, they preferably comprise a sulfur compound which is selected in particular from sodium hydrogensulfite, sodium hydroxymethanesulfinate and the hydrogensulfite adduct of acetone. Additional suitable reducing agents are phosphorus-comprising compounds, such as phosphorous acid, hypophosphites and phosphinates, and also hydrazine or hydrazine hydrate and ascorbic acid. Redox initiator systems can furthermore comprise the addition of small amounts of redox metal salts, such as iron salts, vanadium salts, copper salts, chromium salts or manganese salts, such as, for example, the redox initiator system ascorbic acid/iron(II) sulfate/sodium peroxydisulfate.

The initiator is generally used in an amount of 0.02 to 2% by weight and in particular 0.05 to 1.5% by weight, based on the amount of the monomers M. The optimal amount of initiator naturally depends on the initiator system used and can be determined by a person skilled in the art by routine experiments. The initiator can be partially or completely introduced into the reaction vessel. Preferably, the bulk of the initiator, in particular at least 80%, e.g. 80 to 99.5%, of the initiator, is provided to the polymerization reactor in the course of the polymerization.

The pressure and temperature are of secondary importance for the preparation of the active substance compositions according to the invention. The temperature naturally depends on the initiator system used and an optimal polymerization temperature can be determined by a person skilled in the art through routine experiments. The polymerization temperature usually ranges from 20 to 110° C., frequently from 50 to 95° C. The polymerization is usually carried out at standard pressure or ambient pressure. However, it can also be carried out under increased pressure, e.g. up to 3 bar, or under slightly reduced pressure, e.g. >800 mbar.

The emulsifiers and protective colloids conventionally used for emulsion polymerization which have already been mentioned above as constituents of the active substance formulations according to the invention are suitable as surface-active substances. The amounts of surface-active substances conventionally used for an emulsion polymerization generally lie in the ranges given above, so that all or a portion of the surface-active substances in the compositions according to the invention is supplied via the emulsion polymerization. However, it is also possible to use, in the emulsion polymerization, only a portion, e.g. 10 to 90% by weight, in particular 20 to 80% by weight, of the surface-active substances present in the composition according to the invention and to add the remaining amounts of surface-active substance subsequent to the emulsion polymerization, before or after an optional deodorization of the emulsion polymerization (subsequent saponification).

The molecular weight of the polymers can obviously be adjusted by addition of a small amount of regulators, e.g. 0.01 to 2% by weight, based on the monomers M which are being polymerized. In particular, organic thio compounds and also allyl alcohols and aldehydes are suitable as regulator.

Subsequent to the actual polymerization reaction, it may be necessary to substantially free the aqueous polymer dispersions according to the invention from odorous substances, such as residual monomers and other volatile organic constituents. In a way known per se, this can be achieved physically by distillative removal (in particular via steam distillation) or by stripping with an inert gas. Furthermore, the residual monomers can be lowered chemically by radical postpolymerization, in particular under the effects of redox initiator systems, such as are listed, e.g., in DE-A 44 35 423, DE-A 44 19 518 and DE-A 44 35 422. The postpolymerization is preferably carried out with a redox initiator system composed of at least one organic peroxide and one organic sulfite.

After the end of the polymerization, the polymer dispersions used are frequently, before their use according to the invention, adjusted to an alkaline value, preferably to pH values ranging from 7 to 10. Ammonia or organic amines, and also, preferably, hydroxides, such as sodium hydroxide, potassium hydroxide or calcium hydroxide, can be used for the neutralization.

In this way, stable aqueous polymer dispersions are obtained which comprise, in the polymer particles of the dispersion, at least one fungicidal active substance, and, if appropriate, one or more insecticidal active substances. In addition, the dispersions thus obtained comprise the abovementioned surface-active substances. The active substance preparations thus obtained are characterized by a high stability and a low content of volatile organic compounds, which usually come to not more than 1% by weight, frequently not more than 0.1% by weight and in particular not more than 500 ppm, based on the total weight of the composition. Volatile compounds are, here and subsequently, all organic compounds which exhibit a boiling point of less than 200° C. at standard pressure.

The solids content of the compositions according to the invention is determined to a first approximation by the active substance and the polymer and generally ranges from 10 to 60% by weight and in particular from 20 to 50% by weight.

The active substance compositions thus obtainable can be used directly as such or after diluting. In addition, the compositions according to the invention can also comprise conventional additives, e.g. viscosity-modifying additives (thickeners), antifoam agents, bactericides and antifreeze agents.

Suitable thickeners are compounds which confer a pseudoplastic flow behavior on the formulation, i.e. high viscosity at rest and low viscosity in the agitated state. Mention may be made, in this connection, for example, of polysaccharides or organic layered minerals, such as Xanthan Gum® (Kelzan® from Kelco), Rhodopol® 23 (Rhône-Poulenc) or Veegum® (R. T. Vanderbilt), or Attaclay® (Engelhardt), Xanthan Gum® preferably being used.

Silicone emulsions (such as, e.g., Silicone® SRE, from Wacker, or Rhodorsil® from Rhodia), long-chain alcohols, fatty acids, fluoroorganic compounds and their mixtures, for example, come into consideration as antifoam agents suitable for the dispersions according to the invention.

Bactericides can be added to stabilize the compositions according to the invention from infection by microorganisms. Suitable bactericides are, for example, Proxel® from Avecia (or Arch) or Acticide® RS from Thor Chemie and Kathon® MK from Röhm & Haas.

Suitable antifreeze agents are organic polyols, e.g. ethylene glycol, propylene glycol or glycerol. These are generally used in amounts of not more than 10% by weight, based on the total weight of the active substance composition.

If appropriate, the active substance compositions according to the invention can, to regulate the pH, comprise 1 to 5% by weight of buffer, based on the total amounts of the formulation prepared, the amounts and the type of the buffer used depending on the chemical properties of the active substance or substances. Examples of buffers are alkali metal salts of weak inorganic or organic acids, such as, e.g., phosphoric acid, boric acid, acetic acid, propionic acid, citric acid, fumaric acid, tartaric acid, oxalic acid and succinic acid.

In addition, the aqueous compositions according to the invention can be formulated with conventional binders, for example aqueous polymer dispersions or water-soluble resins, for example water-soluble alkyd resins, or with waxes.

For use in the protection of cellulose-comprising materials, in particular in wood preservation, the aqueous active substance compositions according to the invention can also be formulated with conventional water-soluble wood preservatives, in particular with their aqueous solutions, in order to improve the overall effectiveness against wood-destroying organisms. In this connection, these are, for example, aqueous preparations of conventional wood-protecting salts, for example of salts based on boric acid and alkali metal borates, salts based on quaternary ammonium compounds, e.g. trimethyl- and triethyl($C_6$-$C_{30}$-alkyl)ammonium salts, such as cocotrimethylammonium chloride or trimethylcetylammonium salts, dimethyl- and diethyldi($C_4$-$C_{20}$-alkyl)ammonium salts, such as didecyldimethylammonium chloride, didecyldimethylammonium bromide or dicocodimethylammonium chloride, ($C_1$-$C_{20}$-alkyl)di($C_1$-$C_4$-alkyl)benzylammonium salts, such as cocobenzyldimethyl-ammonium chloride, or methyl- and ethyldi($C_4$-$C_{20}$-alkyl)poly(oxyethyl)-ammonium salts, e.g. didecylmethylpoly(oxyethyl)ammonium chloride and propionate, and also the borates, carbonates, formates, acetates, hydrogencarbonates, sulfates and methyl sulfates, or aqueous preparations of copper-amine complexes, in particular aqueous preparations of salts comprising copper ethanolamine, for example Cu-HDO. Obviously, the aqueous active substance preparations according to the invention can also be formulated with other aqueous fungicidal and insecticidal active substance compositions, for example with conventional emulsion concentrates, suspension concentrates or suspoemulsion concentrates of the abovementioned active substances, e.g. of the abovementioned fungicides from the group of the azoles and of the strobilurins or of the abovementioned insecticides, or with the microemulsions, mentioned at the start, of the abovementioned fungicides and insecticides. By mixing the aqueous active substance composition according to the invention with conventional aqueous preparations of the abovementioned active substances, a broadening in the spectrum of activity is first obtained, if the conventional preparation comprises a different active substance from the aqueous active substance composition according to the invention. Secondly, the advantages of the active substance compositions according to the invention are not lost by formulating with conventional aqueous active substance preparations, in particular the improved adhesion to cellulose-comprising materials and especially to wood. Consequently, the application properties of a conventional aqueous active substance preparation can be improved by formulating with an aqueous active substance composition according to the invention of the same active substance.

There are a number of advantages to the active substance compositions according to the invention. First, these are stable aqueous formulations of fungicidal active substances which are insoluble in water or are soluble in water only to a slight extent. In particular, the phase separation problems observed in conventional formulations and in micro- or nanodispersions of the active substances are not observed and settling of the active substance is not observed, even when drastic conditions are employed, such as occur in the processes employed for impregnating wood with fungicidal active substances. The content of volatile organic compounds is with conventional additivating lower than with comparable conventional formulations and, in comparison to micro- or nanodispersions of active substances, the proportion of emulsifier is simultaneously lower, based on the active substance used. The active substance is leached from the treated material, under the effect of water, to a markedly lesser extent in comparison with other formulations. Furthermore, interactions of the active substances with other formulation constituents or additional active substances, such as frequently occur with a conventional formulation, are not observed. Furthermore, the decomposition of the active substances by the effects of the substrate or environment, such as pH value of the medium or UV radiation, is slowed down or even completely halted. Surprisingly, a reduced effectiveness of the active substance through the incorporation in a polymer matrix is not observed.

The present invention also relates to a process for the protection of cellulose-comprising materials, in particular wood, from infection by harmful fungi, in particular from infection by the abovementioned wood-destroying fungi, in which the cellulose-comprising material, in particular wood, is treated with a composition according to the invention.

Cellulose-comprising materials are, in addition to wood and downstream products, e.g. wood blanks, plywood, chipboard, MDF panels or OSB panels, also pulps and intermediates in the manufacture of paper, fabrics based on cellulose, such as cotton, materials based on woody annuals, for example molded articles formed from rape shavings, bargasse panels, straw panels, and the like. The cellulose-comprising materials furthermore include articles formed from cellulose-comprising fiber materials, such as fabrics, formed fabrics, paper, board, heat-insulating materials, ropes, cables, and the like. Suitable fiber materials for the process according to the invention comprise textile fibers, such as flax, linen, hemp, jute, cotton and ramie, paper fibers, such as flax, linen or hemp, bamboo fibers, paper mulberry and lignocellulose fibers, and also nettle fiber, manila hemp, sisal, kenaf and coconut fiber.

The treatment can be carried out in a way known per se, depending on the type of substrate, by spraying, painting, dipping or impregnating the substrate with an undiluted active substance composition according to the invention or an active substance composition according to the invention diluted with water or by flooding the substrate in an undiluted aqueous active substance composition according to the invention or an aqueous active substance composition according to the invention diluted with water. The compositions according to the invention can also be present in the manufacture of the cellulose-comprising material, for example as binder or as sizing agent.

If the substrate according to the invention is wood, use may be made of the processes conventional in wood preservation, such as are known, for example, from Ullmann's Encyclopedia of Industrial Chemistry, Wood preservation, 5th edition on CD-ROM, Wiley VCH, Weinheim, 1997, chapter 7. These include in particular processes for impregnating the wood with the help of pressure differences, e.g. the vacuum-pressure process and double vacuum impregnation.

The treatment of such materials with the active substance compositions according to the invention can be carried out according to the processes conventional for this and will be adapted in a way known per se to the technical realities in each case. The application concentration and the incorporation depend in this connection on the degree of danger of the material and on the respective treatment process and usually range from 0.05 mg to 10 g of active substance per kg of material.

The undiluted composition comprising the active substance is frequently used in wood downstream products and cellulose-comprising materials, for example together with the binder used, as cobinder. Obviously, separate treatment during or after the manufacture, for example the sizing, is also possible.

In addition to the cellulose-based materials mentioned, the aqueous active substance composition according to the invention can also be used in other areas of material protection from infection by harmful fungi and, if appropriate, from infection by animal pests. For example, skin, fur or leather can be effectively protected, with the aqueous compositions according to the invention, from infection by microorganisms, in particular from infection by the abovementioned harmful fungi, and animal pests. In addition, the aqueous compositions according to the invention can also be used as antifouling paints, for example in shipbuilding, or as algicidal paint systems for facades and roofing tiles, depending on the active substance present therein in each case. In addition, the compositions according to the invention can be used as in-can and film preservatives.

The following examples should clarify the invention, without, however, limiting it:

The viscosities given were determined in a Brookfield rotary viscometer at 23° C. in accordance with ISO 2555.

The particle sizes given were determined by quasielastic light scattering according to the methods described above in diluted dispersions (0.01 to 0.1% by weight). The average diameter, determined by the cumulant analysis of the autocorrelation function measured, is given.

The glass transition temperature was determined in accordance with ASTM D 3418 using differential scanning calorimetry.

I. Preparation of the Active Substance Composition

Example 1a (Aqueous Polymer Dispersion with 3% by Weight of Active Substance, Dispersion D1)

300 g of deionized water and 13.6 g of a 33% by weight aqueous polystyrene dispersion (average particle size 30 nm) were introduced into a reaction vessel equipped with a stirrer, the vessel was flushed with nitrogen and was then heated to 75° C. Beginning simultaneously, feed 1 was added within 3 h and feed 2 was added within 3.15 h, with stirring and while maintaining the temperature. After the end of the addition of feed 2, the temperature was maintained for a further 30 min and then 3.0 g of a 25% by weight aqueous ammonia solution were added. Subsequently, for the purposes of chemical deodorization, feed 3 and feed 4 were added within 90 min while maintaining the temperature and then the reaction mixture was cooled down to ambient temperature. Feed 5 was then added in one portion and the reaction mixture was stirred for 10 min, then adjusted to a pH value of 7 to 7.5 with ammonia and then filtered through a mesh with a mesh size of 125 μm.

The dispersion obtained had a solids content of 38.7% by weight and a viscosity of 30 mPa·s. The glass transition temperature of the polymer was +16° C. The average particle size, determined by means of light scattering, was 146 nm.

Feed 1:
400.0 g of deionized water
25.7 g of a 28% by weight solution of an anionic emulsifier E1[1)]
21.0 g of a 28% by weight solution of a nonionic emulsifier E2[2)]
7.8 g of acrylic acid
292.0 g of styrene
237.0 g of n-butyl acrylate
60.0 g of ethyl acrylate
3.0 g of acrylamide
18.0 g of epoxiconazole Feed 2:
100 g of deionized water
2.4 g of sodium peroxodisulfate Feed 3:
22.0 g of deionized water
2.6 g of t-butyl hydroperoxide (70% by weight)

Feed 4:
25.0 g of deionized water
1.7 g of sodium hydroxymethanesulfinate

Feed 5:
37.0 g of deionized water
30.0 g of emulsifier solution E2

1) sodium lauryl sulfate
2) $C_{16}/C_{18}$ fatty alcohol ethoxylate with on average 18 ethylene oxide units per molecule

Example 1b (Aqueous Polymer Dispersion with 2% by Weight of Fungicidal Active Substance and 1% by Weight of Insecticidal Active Substance, Dispersion D2)

The preparation was carried out analogously to the procedure of example 1a, feed 1 having the following composition:

Feed 1:
400.0 g of deionized water
25.7 g of a 28% by weight solution of an anionic emulsifier E1[1)]
21.0 g of a 28% by weight solution of a nonionic emulsifier E2[2)]
7.8 g of acrylic acid
322.0 g of styrene
177.0 g of n-butyl acrylate
60.0 g of ethyl acrylate
30.0 g of acrylonitrile
3.0 g of acrylamide
12.0 g of epoxiconazole
6.0 g of chlorfenapyr The dispersion obtained had a solids content of 39% by weight and a viscosity of 45 mPa·s. The glass transition temperature of the polymer was 31° C. The average particle size, determined by means of light scattering, was 151 nm.

Example 2 (Step Polymers with Different Active Substances, Dispersions D3 to D8)

General Procedure:
183 g of water and 75.8 g of an aqueous polystyrene dispersion (33% by weight, average particle diameter 30 nm) were introduced into a reaction vessel, the vessel was flushed with nitrogen and was heated to 85° C. 25% by weight of a solution of 1.5 g of sodium peroxodisulfate in 21.4 g of water (feed 4) were added hereto while maintaining the temperature. After 10 min, beginning simultaneously, the addition of feed 1 and the addition of the remaining amount of feed 4 were commenced. Feed 1 was added within 90 min while maintaining the temperature, feed 4 within 255 min. After the end of the addition of feed 1, the temperature was maintained for 30 min, then feed 2 was added within 60 min, the temperature was maintained for a further 45 min and then feed 3 was added within 30 min while maintaining the temperature. After the end of the addition of feed 3, the temperature was maintained for a further 30 min and then the reaction mixture was cooled to ambient temperature.

Feed 1:
220.1 g of water
220.8 g of styrene
1.6 g of allyl methacrylate
11.1 g of emulsifier solution E3
x g of active substance (see table 1)

Feed 2:
135.6 g of water
180.4 g of n-butyl acrylate
2.1 g of allyl methacrylate
7.2 g of emulsifier solution E3
y g of active substance (see table 1)

Feed 3:
92.5 g of water
19.7 g of styrene
75.5 g of methyl methacrylate
1.7 g of emulsifier solution E3
z g of active substance (see table 1)

Emulsifier solution E3: 45% by weight aqueous solution of a sodium salt of ($C_{16}$-alkyl)-diphenyl ether sulfonic acid

TABLE 1

| Dispersion | Active substance | x [g] | y [g] | z [g] |
|---|---|---|---|---|
| D3 | Metconazole | 26.4 | 14.4 | 12.0 |
| D4 | Cyproconazole | 21.6 | 10.8 | 10.8 |
| D5 | Epoxiconazole | 30.0 | 6.0 | 6.0 |
| D6 | Tebuconazole | 15.0 | 18.0 | — |
| D7 | IPBC[1)] | 21.0 | 4.2 | 6.0 |
| D8 | Epoxiconazole + Chlorfenapyr | 4.0 2.0 | 4.0 2.0 | 4.0 2.0 |

1) IPBC=3-iodo-2-propyl butylcarbamate.

The dispersions obtained had a solids content of 45% by weight and a viscosity of 115 mPa·s. The polymer showed 2 glass transition temperatures at −31 and +99° C. determined by means of DSC. The average particle size, determined by means of light scattering, was 95 to 105 nm.

Example 3 (Cationic Dispersions D9-D13 with Different Active Substances)

General Preparation Procedure:
465 g of deionized water, 5% by weight of feed 1 and 10% by weight of feed 2 were heated to 80° C. After 10 min, the addition of the remaining amounts of feed 1 and feed 2 was commenced. The feed time was 3.5 h. After the end of the addition of the feeds, the mixture was maintained at 80° C. for a further 30 min and was cooled down to ambient temperature.

Feed 1:
496.1 g of deionized water
7.6 g of sulfuric acid (50% by weight)

361.0 g of methyl methacrylate
19.0 g of dimethylaminoethyl methacrylate
57.0 g of emulsifier solution E4
x g of active substance (see table 2)
Feed 2:
Solution of 1.5 g of 2,2'-azobis(N,N'-dimethylisobutyramidine) in 63.3 g of Deionized Water
Emulsifier solution E4: 40% by weight aqueous solution of a cationic emulsifier obtained by successive ethoxylation of stearylamine with 4-5 mol of ethylene oxide and subsequent quatemization with dimethyl sulfate.

TABLE 2

| Dispersion | Active substance | x [g] |
|---|---|---|
| D9 | Metconazole | 61.8 |
| D10 | Cyproconazole | 42.9 |
| D11 | Epoxiconazole | 0.4 |
| D12 | Tebuconazole | 19.0 |
| D13 | IPBC | 18.2 |

The dispersion obtained had a solids content of 29.5% by weight and a viscosity of 100 mPa·s. The polymer showed a glass transition temperature at 87° C. determined by means of DSC. The average particle size, determined by means of light scattering, was 157 to 175 nm.

Example 4 (Cationic Dispersions D14-D18 with Different Active Substances)

General Preparation Procedure:
465 g of deionized water, feed 1 and 10% by weight of feed 2 were heated to 80° C. After 10 min, the addition of the remaining amount of feed 2 and of feed 3 was begun. The feed time of feed 2 and feed was 3.5 h. After the end of the addition of the feeds, the mixture was maintained at 80° C. for a further 30 min and was then cooled down to ambient temperature.
Feed 1:
46.1 g of deionized water
38.0 g of styrene
7.6 g of 3-(N,N-dimethylamino)propylmethacrylamide
14.2 g of emulsifier solution E4 (see above)
Feed 2:
Solution of 1.5 g of 2,2'-azobis(N,N'-dimethylisobutyramidine) in 63.3 g of Deionized Water
Feed 3:
450.1 g of deionized water
7.6 g of acrylic acid
270.0 g of methyl methacrylate
57.0 g of dimethylaminoethyl methacrylate
42.8 g of emulsifier solution E4 (see above)
x g of active substance (see table 3)

TABLE 3

| Dispersion | Active substance | x [g] |
|---|---|---|
| D14 | Metconazole | 61.8 |
| D15 | Cyproconazole | 42.9 |
| D16 | Epoxiconazole | 0.4 |
| D17 | Tebuconazole | 19.0 |
| D18 | IPBC[1) ] | 18.2 |

The dispersion obtained had a solids content of 29.8% by weight and a viscosity of 105 mPa·s. The polymer showed a glass transition temperature at 110° C. determined by means of DSC. The average particle size, determined by means of light scattering, was 155 to 175 nm.

II. Application Investigation

The limits of the effectiveness of the compositions according to the invention with regard to wood-destroying basidiomycetes were determined on wood test specimens of *Pinus* spp. (southern yellow pine) with the dimensions 40×15×4 mm. The test method on comminuted wood test specimens, known as the Bravery test, is closely based on EN 113 and is used to determine the preventive effect of wood preservatives against wood-destroying fungi (see in this connection A. F. Bravery, Intern. Res. Group Wood Pres., Doc. No. IRG/WP/2113, 5S., Stockholm, 1978). The wood test specimens impregnated with the composition according to the invention were tested without or with the constraint of leaching according to EN 84. The investigation was carried out with 6 different active substance concentrations ranging from 0.4 to 4% by weight of active substance (with epoxiconazole) or 0.63 to 6.3% by weight of active substance (with tebuconazole) and each time 5 parallel test specimens per active substance concentration and test fungus. *Coniophora puteana* BAM Ebw. 15 and *Poria placenta* FPRL 280 were used as test fungi. The destruction of the wood caused by fungal infection was registered by the loss in weight of the test woods, which was determined after 6 weeks. If the loss in weight is less than 3% by weight, based on the starting dry weight of the test sample, the protection of the wood achieved by the preservative at a particular active substance concentration is regarded as satisfactory. The concentration limit of the effectiveness is given in two concentrations. The lower concentration gives the value at which the wood is no longer satisfactorily protected and the higher concentration corresponds to the minimum concentration with which complete protection is achieved.

A dispersion with an active substance content of 5.52% by weight of epoxiconazole (based on the solids content, or 2.4% by weight, based on the dispersion), a solids content of 43.7% by weight and an average particle size of 107 nm, prepared according to the procedure in example 2, and a dispersion with an active substance content of 4.69% by weight of tebuconazole (based on the solids content, or 2.05% by weight, based on the dispersion), a solids content of 43.8% by weight and an average particle size of 98 nm, prepared according to the procedure in example 2, were tested.

The limits of the effectiveness are represented in table 4. For comparison, the values determined for a solution of the active substance in acetone are given.

TABLE 4

| | Limits of the effectiveness [kg/m$^3$] | |
|---|---|---|
| Test fungus | Without leaching | With leaching (EN 84) |
| Dispersion with epoxiconazole | | |
| CP | <0.066 | <0.066 |
| PP | <0.066 | <0.066 |
| Solution of epoxiconazole | | |
| CP | <0.19 | 0.11-0.16 |
| PP | <0.19 | 0.11-0.18 |
| Dispersion with tebuconazole | | |
| CP | <0.092 | <0.089 |
| PP | 0.091-0.143 | <0.092 |

TABLE 4-continued

| | Limits of the effectiveness [kg/m³] | |
|---|---|---|
| Test fungus | Without leaching | With leaching (EN 84) |
| | Solution of tebuconazole | |
| CP | <0.052 | <0.054 |
| PP | 0.102-0.153 | 0.095-0.152 |

In practice, the upper value after leaching in particular is decisive for the assessment of a wood preservative. The results represented in table 4 prove that the active substance compositions according to the invention show an effectiveness against wood-destroying fungi which is at least comparable to, in the case of epoxiconazole even better than, that of formulations in organic solvents.

Wood test specimens which, for control purposes, were treated only with a dispersion free of active substance with otherwise an identical composition showed, under test conditions, serious damage to the wood substance by fungal infection which was only slightly less than with untreated wood test samples.

What is claimed is:

1. A process for the protection of cellulose-comprising materials from infection by microorganisms comprising the treatment of the cellulose-comprising material with an aqueous active substance composition, said composition comprising (a) at least one fungicidal organic active substance with a solubility in water of less than 1 g/l at 25° C./1013 mbar, and (b) a finely-divided polymer with an average particle size, determined by dynamic light scattering, of 10 to 250 nm, in which the polymer particles comprise the active substance, the polymer having a glass transition temperature of at least 10° C. and being formed from ethylenically unsaturated monomers M consisting of:

from 70 to 99.5% by weight, based on the total amount of the monomers M, of at least one neutral monoethylenically unsaturated monomer M1 with a solubility in water of not more than 30 g/l at 25° C., which is selected from styrene and esters of monoethylenically unsaturated mono- or dicarboxylic acids with C1-C10-alkanols or C5-C8-cycloalkanols, and from 0.50 to 30% by weight, based on the total amount of the monomers M, of at least one ethylenically unsaturated monomers M2, which is selected from:

monoethylenically unsaturated monomers M2a exhibiting at least one acid group or at least one anionic group, the amount of monomers M2a being not more than 20% by weight, based on the total amount of the monomers M;

monoethylenically unsaturated neutral monomers M2b exhibiting a solubility in water of at least 50 g/l at 25° C., the amount of monomers M2b being not more than 10% by weight, based on the total amount of the monomers M; and not more than 2% by weight, based on the total amount of the monomers M, of monomers having two or more nonconjugated ethylenically unsaturated double bonds, wherein the aqueous active substance composition is obtained by a process comprising radical aqueous emulsion polymerization of an oil-in-water emulsion of the monomers M, the monomer droplets of the oil-in-water emulsion to be polymerized comprising the fungicidal active substance in dissolved form.

2. The process according to claim 1, wherein the cellulose-comprising material is wood.

3. The process according to claim 1, wherein the monomers M1 are selected from styrene, C2-C10-alkyl acrylates and C1-C10-alkyl methacrylates.

4. The process according to claim 1, wherein the polymer exhibits a glass transition temperature TG of at least 30° C.

5. The process according to claim 1, wherein the aqueous active substance composition comprises at least one fungicidally active substance in an amount of 0.1 to 50% by weight, based on the weight of the monomers M used for the preparation of the polymer.

6. The process according to claim 5, wherein the fungicidally active substance is selected from the fungicides from the group of the conazoles, the group of the morpholines, the group of the strobilurins, the group of the thiazoles, the group of the sulfenamides and the group of the iodine compounds.

7. The process according to claim 1, where the polymer particles additionally comprise an insecticidally active substance.

8. The process according to claim 7, wherein the insecticidal active substance is selected from pyrethroids, arthropod growth regulators, chlorfenapyr and neonicotinoids.

9. The process according to claim 1, where the total amount of active substance is 0-5 to 50% by weight, based on the total amount of the monomers M.

10. The process according to claim 1, where the aqueous active substance composition has a content of volatile organic constituents of less than 1% by weight, based on the total weight of the composition.

11. The process according to claim 1, wherein the aqueous active substance composition has a solids content of 10 to 60% by weight.

* * * * *